(12) United States Patent
Pinchuk

(10) Patent No.: US 7,559,952 B2
(45) Date of Patent: Jul. 14, 2009

(54) ELASTOMERIC POLYMER FILAMENT COSMETIC IMPLANT

(75) Inventor: Leonard Pinchuk, Miami, FL (US)

(73) Assignee: Innovia, LLC, Miami, FL (US)

( * ) Notice: Subject to any disclaimer, the term of this patent is extended or adjusted under 35 U.S.C. 154(b) by 504 days.

(21) Appl. No.: 11/015,941

(22) Filed: Dec. 17, 2004

(65) Prior Publication Data

US 2006/0136070 A1    Jun. 22, 2006

(51) Int. Cl.
*A61F 2/02* (2006.01)
(52) U.S. Cl. .................................................. 623/23.72
(58) Field of Classification Search .............. 623/23.72; 606/228–231
See application file for complete search history.

(56) References Cited

U.S. PATENT DOCUMENTS

| | | | |
|---|---|---|---|
| 3,194,239 A * | 7/1965 | Sullivan | 606/228 |
| 3,454,011 A * | 7/1969 | Wagner | 606/224 |
| 3,921,636 A * | 11/1975 | Zaffaroni | 424/432 |
| 3,981,307 A | 9/1976 | Borysko | |
| 4,263,913 A | 4/1981 | Malmin | |
| 4,805,292 A * | 2/1989 | Noguchi | 29/445 |
| 4,880,002 A * | 11/1989 | MacGregor | 606/226 |
| 4,965,071 A | 10/1990 | Kawan | 424/401 |
| 5,397,352 A | 3/1995 | Burres | 623/11 |
| 5,713,375 A | 2/1998 | McAllister | 128/898 |
| 5,741,331 A | 4/1998 | Pinchuk | |
| 5,895,413 A | 4/1999 | Nordstrom | |
| 6,086,578 A * | 7/2000 | Adamyan et al. | 606/1 |
| 6,102,939 A | 8/2000 | Pinchuk | |
| 6,197,043 B1 | 3/2001 | Davidson | 606/228 |
| 6,197,240 B1 | 3/2001 | Pinchuk | |
| 6,203,564 B1 | 3/2001 | Hutton et al. | 606/228 |
| 6,545,097 B2 | 4/2003 | Pinchuk et al. | |
| 6,855,770 B2 | 2/2005 | Pinchuk et al. | |
| 2003/0235602 A1 * | 12/2003 | Schwarz | 424/424 |
| 2007/0167958 A1 * | 7/2007 | Sulamanidze et al. | 606/139 |

FOREIGN PATENT DOCUMENTS

| | | |
|---|---|---|
| EP | 0140557 | 5/1995 |
| EP | 1 075 843 A1 | 2/2001 |
| FR | 2796833 | 2/2001 |

(Continued)

OTHER PUBLICATIONS

Sculptra (article/ad); by Dermik Aesthetics; 2004; downloaded from Internet (www1.sculptra.com); for the restoration of facial aging.

(Continued)

*Primary Examiner*—(Jackie) Tan-Uyen T. Ho
*Assistant Examiner*—Gregory A Anderson
(74) *Attorney, Agent, or Firm*—Gordon & Jacobson, PC

(57) ABSTRACT

A cosmetic implant comprises a filament made from a biocompatible elastomer. The elastomeric filament can be injected or pulled under one or more wrinkles. Once implanted under the wrinkle(s), the filament lifts and supports the tissue above it. Such lifting lessens (and possibly removes altogether) the appearance of the wrinkle(s). The biocompatible elastomeric filament is preferably made from a polyolefinic copolymer material having a triblock polymer backbone comprising polystyrene-polyisobutylene-polystyrene, which is herein referred to as "SIBS"; or alternatively can be made from silicon rubber, expanded polytetrafluorethelyene (ePTFE), polyurethane, polyolefin, copolymers of nylon, copolymers of polyester, or elastin.

12 Claims, 4 Drawing Sheets

FOREIGN PATENT DOCUMENTS

| WO | WO 98/37836 | 9/1998 |
|---|---|---|
| WO | WO 00/51658 | 9/2000 |
| WO | WO02/47731 | 6/2002 |
| WO | WO 03/103972 | 12/2003 |

OTHER PUBLICATIONS

Restylane (article/ad); by Medicis Aesthetics Holdings, Inc.; 2004 downloaded from Internet (www.restylaneusa.com); a cosmetic dermal filler.

Hylaform (article/ad); Looking Your Best.com; 2004; a dermal filler made from purified hyaluronic acid.

Contour Threads (article/ad); Quill Medical, Inc./Surgical Specialties Corp.; 2004; downloaded from Internet (www.contourthreads.com).

A non-surgical approach to lifting skin for a rejuvenated appearance. Feather Lift; by Meso Beauty Cosmetic Health Institute; 2003; downloaded from Internet (www.mesobeauty.com); Facial Lifting with Aptos Threads.

Curl Lift (article/ad); Cosmetic Surgery News; Skin Store.com; 2004;a non-surgical procedure using a needle and thread for facial restoration.

Aptos Threads (article/ad); FeatherLift; Robin Berger, MD—435-673-7546.

Suture Needles Ad; Barber of Sheffield Ltd.; types of shapes and points.

* cited by examiner

ELASTOMERIC POLYMER FILAMENT COSMETIC IMPLANT

BACKGROUND OF THE INVENTION

1. Field of the Invention

This invention relates broadly to skin rejuvenation. More particularly, this invention relates to methods, devices, techniques and materials for skin rejuvenation.

2. State of the Art

There are many known techniques for skin rejuvenation (the removal or lessening of the appearance of wrinkles and/or folds on the skin and/or sagging skin) including surgical skin tightening, less-evasive subcutaneous skin tightening and dermal fillers.

As part of surgical skin tightening, the skin is incised in an area that is adjacent the wrinkled skin. Additional skin peeling is performed. Finally, the skin is tightened and the excess is cut off. Such techniques are disadvantageous due to the high trauma involved and a high risk of post-operative adverse side effects (such as hematomas and scar complications).

Less evasive subcutaneous skin tightening employs a surgical thread to gather and tighten wrinkled or sagging skin. For example, European Patent No. 1075843 discloses the use of a barbed surgical thread in cosmetic applications. The barbs of the thread are oriented in a direction opposite that of thread pull. The thread is made of metallic, polymeric or biological materials. This type of thread, made from polypropylene, is used commercially under the name FeatherLift™ to provide skin tightening. The thread is inserted under the skin generally perpendicular to and extending away from the wrinkles or sagging skin. The barbs at one end of the thread anchor themselves to the skin at or near the winkles or sagging area. The other end of the thread is pulled tight and tied to tissue (e.g., the facia of the head), thereby gathering and tightening the skin in a manner that lessens the appearance of the wrinkles or sagging skin.

A dermal filler is a biocompatible material that is injected into the skin. These fillers include collagen, silicone, colloidal microspheres of PMMA, colloidal microspheres of PTFE (Teflon®) and colloidal hydroxyapatite. Collagen injections, which are most popular, suffer from the collagen degrading with time, resulting in numerous visits to the plastic surgeon for re-injection. Furthermore, collagen is hypoallergenic and approximately seven percent of the population suffers from these allergies. In addition, collagen from bovine origin can carry prions from mad cow disease which can be deadly to the patient. Silicone as well as PMMA and Teflon microspheres do not degrade, however they all do tend to migrate from the injection site. The microspheres are at times found as far away as the lymph nodes. Hydroxysapatite injections are forerunners to bone formation and tend to harden with time. More recently, dermal fillers such as Restylane® (hyaluronic acid), Hylaform®) (hyaluronic acid) and Sculptra™ (poly-L-lactic acid) have been introduced for cosmetic applications. All of these fillers are helpful but temporary in nature. Moreover, if injected incorrectly, they are non-removable and therefore cannot be corrected.

SUMMARY OF THE INVENTION

It is therefore an object of the invention to provide a cosmetic implant that provides for permanent lifting of the tissue under the skin.

It is another object of the invention to provide such a cosmetic implant that affords minimal tissue damage and minimal adverse post-operative side effects (pain, bruising, and other discoloration).

It is a further object of the invention to provide such as cosmetic implant that is safe and simple to use.

It is another object of the invention to provide such as cosmetic implant that is inexpensive to manufacture.

In accord with these objects, which will be discussed in detail below, a cosmetic implant is provided that comprises a filament made from a biocompatible elastomer. The elastomeric filament can be injected or pulled under one or more wrinkles. Once implanted under the wrinkle(s), the filament lifts and supports the tissue above it. Such lifting lessens (and possibly removes altogether) the appearance of the wrinkle (s). The biocompatible elastomeric filament can be made from silicon rubber, expanded polytetrafluorethelyene (ePTFE, also called GORE-TEX®), polyurethane, polyolefin, copolymers of nylon, copolymers of polyester, elastin, or a polyolefinic copolymer material having a triblock polymer backbone comprising polystyrene-polyisobutylene-polystyrene, which is herein referred to as "SIBS".

According to one embodiment of the invention, the filament is secured to a needle by crimping or by an eyelet. The needle is adapted to be inserted under the surface of the skin. The filament is preferably inserted under a wrinkle, and the filament is pulled therethrough such that it extends lengthwise under the wrinkle.

According to another embodiment of the invention, the filament is delivered from inside a hollow needle. The hollow needle is adapted to be inserted into the skin under the wrinkle, and the filament is deployed therefrom.

According to yet another embodiment of the invention, the filament is formed in situ in the skin under the wrinkle.

Additional objects and advantages of the invention will become apparent to those skilled in the art upon reference to the detailed description taken in conjunction with the provided figures.

BRIEF DESCRIPTION OF THE DRAWINGS

FIG. 8A is a schematic cross-section view transverse to the wrinkle before implantation. FIG. 8B is a schematic side view along the longitudinal direction of the wrinkle after implantation. FIG. 8C is a schematic cross-section view transverse to wrinkle after implantation.

DETAILED DESCRIPTION

Figure 1:
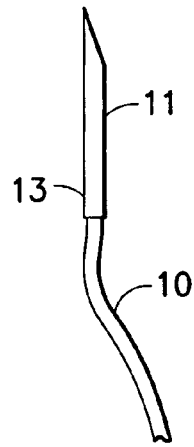
FIG. 1 is a schematic illustration of a cosmetic implant system in accordance with the present invention, including a needle and an elastomeric filament implant secured thereto.

The present invention is a cosmetic implant 10 that lessens (and possibly removes altogether) the appearance of one or more wrinkles on the skin. The cosmetic implant 10 comprises a filament made from a biocompatible elastomer preferably having elasticity along its length between 200 percent and 1500 percent. In other words, a given length of the elastomeric filament is capable of being stretched between two and fifteen times its given length. The elastomeric filament can be injected or pulled under one or more wrinkles. Once implanted under the wrinkle(s), the filament forms a permanent support structure for the tissue above it, thereby lifting and contouring the skin. Such lifting lessens (and possibly removes altogether) the appearance of the wrinkle(s). The cosmetic implant 10 can also be implanted under folds and/or sagging skin to lift the skin as desired. In the preferred embodiment, the biocompatible elastomeric filament is made from a polyolefinic copolymer material having a triblock polymer backbone comprising polystyrene-polyisobutylene-polystyrene, which is herein referred to as "SIBS". Alternatively, the biocompatible elastomeric filament can be made from silicon rubber, expanded polytetrafluorethelyene (ePTFE, also called GORE-TEX™), polyurethane, polyolefin, copolymers of nylon, copolymers of polyester, or elastin. Preferably, the elastomeric filament is formed by extrusion.

Non-cross linked high molecular weight polyisobutylene (PIB) is a soft putty-like material with a Shore hardness less than 20A. When copolymerized with polystyrene, it can be made at hardnesses ranging up to the hardness of polystyrene, which has a Shore hardness of 100D. Thus, depending on the relative amounts of styrene and isobutylene, the SIBS material can have a range of hardnesses from as soft as Shore 10A to as hard as Shore 100D. In this manner, the SIBS material can be adapted to have the desired elastomeric and hardness qualities. For example, the filament formed from SIBS material with 25 mole percent styrene provides an elasticity of 200% along its length. In another example, the filament formed from SIBS material with 5 mole percent styrene provides an elasticity of 1500% along its length. Details of the SIBS material is set forth in U.S. Pat. Nos. 5,741,331; 6,102,939; 6,197,240; 6,545,097, which are hereby incorporated by reference in their entirety.

The SIBS material of the elastomeric filament may be polymerized under control means using carbocationic polymerization techniques such as those described in U.S. Pat. Nos. 4,276,394; 4,316,973; 4,342,849; 4,910,321; 4,929,683; 4,946,899; 5,066,730; 5,122,572; and Re 34,640, each herein incorporated by reference in its entirety. The amount of styrene in the copolymer material is preferably between about 15 mole percent to 5 mole percent for the desired elasticity range between 200% and 1500% as described herein. The styrene and isobutylene copolymer materials are preferably copolymerized in solvents.

In accord with another aspect of the invention, it is expected that alternative polymeric materials are suitable for the practice of the present invention. Such alternative polymeric materials preferably include polyisobutylene-based material capped with a glassy segment. The glassy segment provides hard domains for the elastomeric polyisobutylene and is non-reactive in the body. The glassy segment preferably does not contain any cleavable group which will release in the presence of body fluid and cause toxic side effects. The glassy segment can be a vinyl aromatic polymer (such as polystyrene, α-methylstyrene, or a mixture thereof), or a methacrylate polymer (such as methylmethacrylate, ethylmethacrylate, hydroxymethalcrylate, or a mixture thereof). Such materials preferably have a general block structure with a central elastomeric polyolefinic block and thermoplastic end blocks. Even more preferably, such materials have a general structure:

BAB or ABA (linear triblock),
B(AB)n or A(BA)n (linear alternating block), or
X-(AB)n or X-(BA)n (includes diblock, triblock and other radial block copolymers),
where A is an elastomeric polyolefinic block, B is a thermoplastic block, n is a positive whole number and X is a starting seed molecule.

Such materials may be star-shaped block copolymers (where n=3 or more) or multi-dendrite-shaped block copolymers.

Figure 2A:
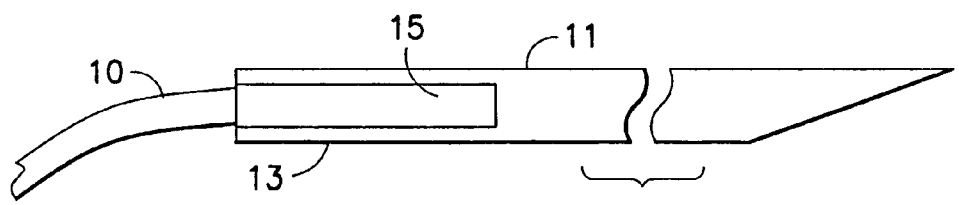
FIGS. 2A and 2B are schematic illustrations of an exemplary embodiment of a cosmetic implant system in accordance with the present invention, wherein the filament is inserting into a bore in the needle and crimped for fixation therein.
Figure 2B:
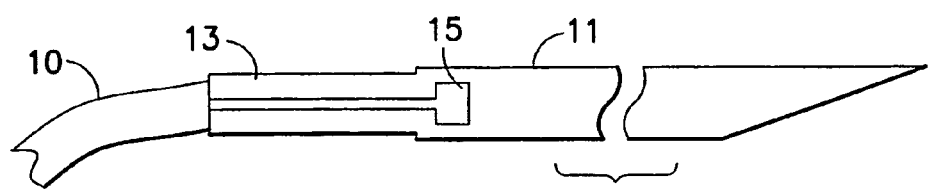

Turning now to FIG. 1, there is shown a schematic diagram of a needle 11 with the elastomeric filament implant 10 secured to the distal end 13 of the needle 11. The elastomeric filament implant 10 can be secured to the distal end 13 with a bore 15 formed in the needle 11. The bore 15 is sized at a diameter slightly larger than the diameter of the filament implant 10 as shown in FIG. 2A. The filament implant 10 is placed into the bore 15, and a crimping machine is used to cause the material surrounding the bore 15 to elastically deform and crimp down on the filament implant 10 therein as shown in FIG. 2B.

Figure 3:
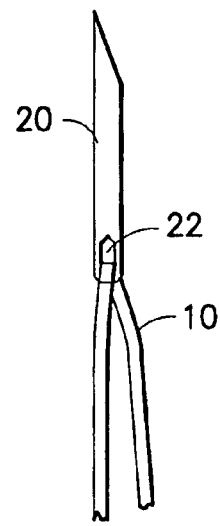
FIG. 3 is a schematic illustration of a cosmetic implant system in accordance with the present invention, including a needle and an elastomeric filament implant that is received through an eyelet of the needle.
Figure 4A:
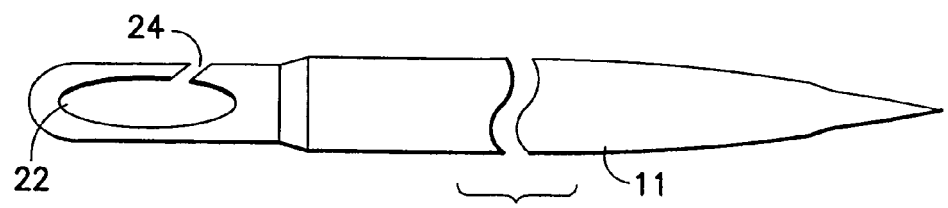
FIGS. 4A through 4D are schematic illustrations of an exemplary embodiment of a cosmetic implant system in accordance with the present invention, wherein the filament is inserted through a slit in the eyelet of a needle for support therein.
Figure 4B:
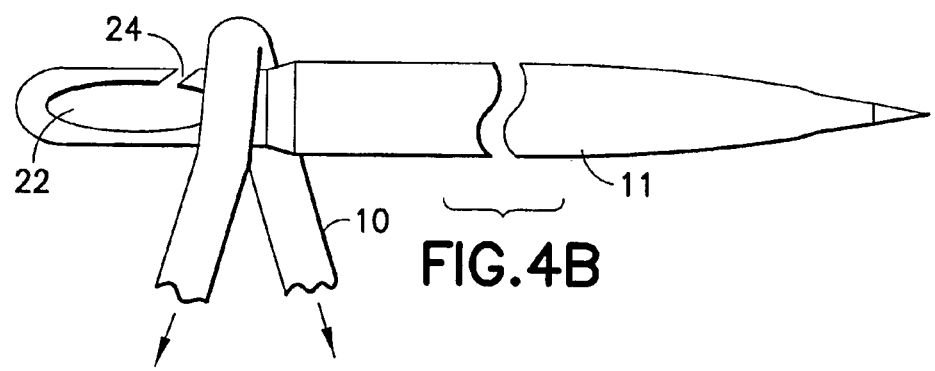
Figure 4C:
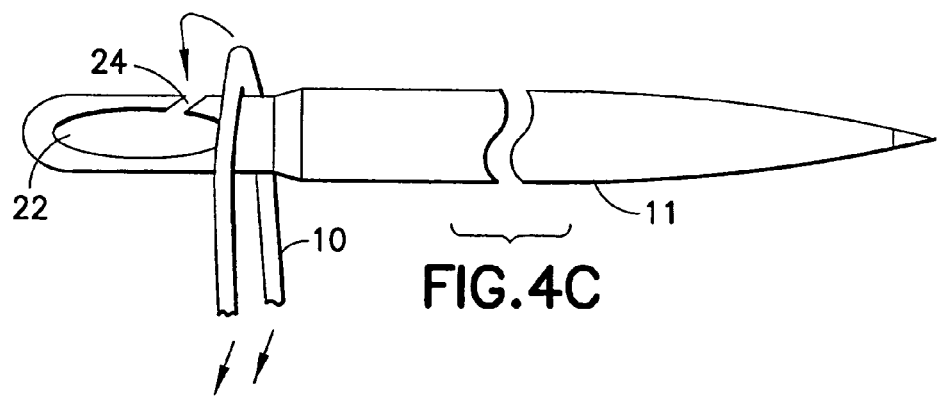
Figure 4D:
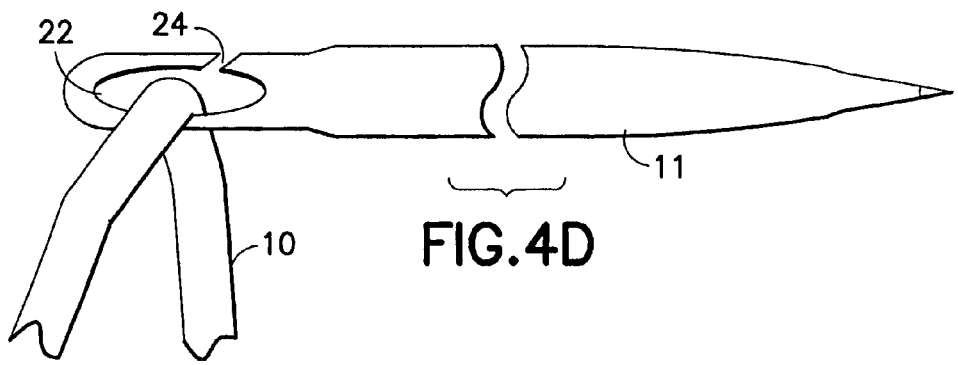

FIG. 3 illustrates an alternate embodiment wherein the filament implant 10 is threaded through an eyelet 22 in a needle 20. The eyelet 22 can form a complete loop as shown in FIG. 3. Alternatively, the eyelet 22 can have a slit 24 as shown FIGS. 4A through 4D. Preferably, the slit 24 has a width that is smaller than the diameter of the filament implant 10 (FIG. 4A). In order to attach the filament implant 10 to the needle 20, the slit 24 is placed under a loop of the filament implant 10 (FIG. 4B). The filament implant loop is pulled until the loop necks down in diameter (due to its elastomeric nature) such that it can pass through the slit 24 and into the eyelet 22 (FIG. 4C). The necked down loop is then pulled through the slit 24 and into the eyelet 22. Once in the eyelet 22, the filament implant is relaxed which causes it to expand back to its original diameter where it remains trapped and cannot pass out through the slit 24 (FIG. 4D).

In the embodiments of FIG. 1 through 4D, the filament implant 10 is secured to the needle 11 (which may be straight or slightly curved). The needle 11 is tunneled longitudinally under the wrinkle. In other words, the needle 11 is inserted under the wrinkle at one end and emerges at the other longitudinal end of the wrinkle. The needle is pulled out of the skin and the filament implant 10 is pulled until it is totally under the wrinkle (i.e., the wrinkle is "flossed" with the filament implant 10). The filament implant 10 is then held in place (preferably by applying finger pressure to the skin above the middle of the filament implant 10), and then stretched slightly on each end and cut. In this manner, after being cut the stretched filament implant 10 retracts back a small distance into the wound under the wrinkle. This allows the wound to heal without the filament implant 10 sticking out of the wound. When implanted under the wrinkle, the filament implant 10 provides a permanent support structure for the tissue above it, thereby lifting and contouring the skin. Such lifting lessens (and possibly removes altogether) the appearance of the wrinkle. The filament implant 10 can also be implanted under folds and/or sagging skin to lift the skin as desired.

Figure 5:
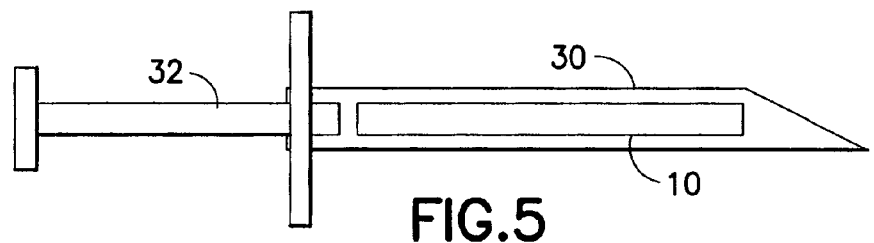
FIG. 5 is a schematic illustration of a cosmetic implant system in accordance with the present invention, including a hollow needle and an elastomeric filament implant disposed therein.

FIG. 5 illustrates an alternate embodiment wherein the filament implant 10 is held inside a hollow needle 30 with a plunger 32. The needle 30 is inserted under the wrinkle and the plunger 32 held in place while the needle 30 is retracted, thereby leaving the filament implant 10 in place under the wrinkle. When implanted under the wrinkle, the filament implant 10 provides a permanent support structure for the tissue above it, thereby lifting and contouring the skin. Such lifting lessens (and possibly removes altogether) the appearance of the wrinkle. The filament implant 10 can also be implanted under folds and/or sagging skin to lift the skin as desired.

Figure 6:
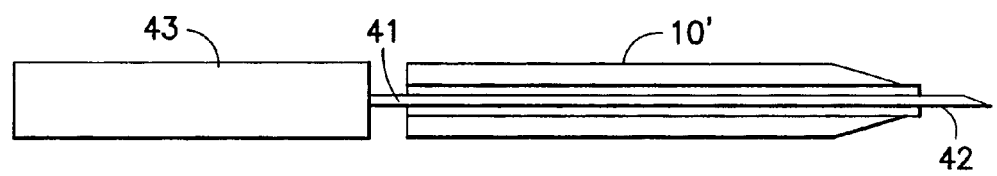
FIG. 6 is a schematic illustration of a cosmetic implant system in accordance with the present invention, including a hollow filament implant disposed around a delivery needle.

FIG. 6 illustrates another alternate embodiment where the elastomeric implant 10' is hollow. The hollow implant 10' fits over a stylet 41. The stylet 41 has a handle 43 and a tip 42 that emerges from the hollow implant 10'. The tip 42 is sufficiently sharp to allow tunneling under the wrinkle. The stylet 41 together with the hollow implant 10' is inserted under the wrinkle. Once the hollow implant 10' is located under the wrinkle, the stylet 41 is removed by grasping handle 43 and pressing against the hollow implant 10'. When implanted under the wrinkle, the hollow implant 10' provides a permanent support structure for the tissue above it, thereby lifting and contouring the skin. Such lifting lessens (and possibly removes altogether) the appearance of the wrinkle. The filament implant 10 can also be implanted under folds and/or sagging skin to lift the skin as desired.

Figure 7:
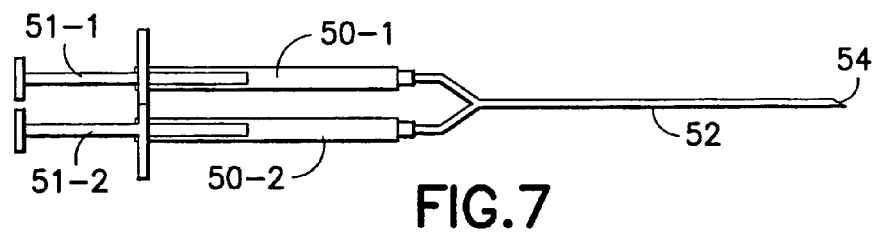
FIG. 7 is a schematic illustration of a cosmetic implant system in accordance with the present invention, including multiple syringes that house different chemicals that are mixed and react in a needle element to form an elastomeric filament implant in situ for delivery from the needle element.

In alternate embodiments, an elastomeric filament implant 10" may be formed in situ. FIG. 7 illustrates an exemplary system that forms the elastomeric filament implant 10" in situ. It includes a first syringe 50-1 and a second syringe 50-2 that are dispensed by plungers 51-1 and 51-2, respectively, such that the material held in the two syringes converge in a needle element 52 where it mixes and polymerizes into the filament implant 10" that is dispensed from the tip 54 of the needle element 52. The material held in the two syringes can be selected from a wide variety of biocompatible polymeric systems. For example, a polyurethane filament implant can be formed with the first syringe 50-1 containing a diisocynate terminated prepolymer and the second syringe 50-2 containing a diol or diamine terminated molecule. In the system, when the material from the two syringes mix, the alcohol or amine groups of the material of the second syringe 50-2 immediately react with the isocyanate groups of the first syringe 50-1 to form a high molecular weight elastomeric polyurethane or polyurethane urea. The tip 54 is sufficiently sharp to allow tunneling under the wrinkle. In use, the needle element 52 is inserted under the wrinkle and the plungers 51-1 and 51-2 are pushed into the syringes 50-1 and 50-2, respectively, which causes the material held in the two syringes to converge in the needle element 52 where it mixes and polymerizes to form the filament implant 10". The filament implant 10" is dispensed from the tip 54 of the needle element 52 under the wrinkle to provide a permanent support structure for the tissue above it, thereby lifting and contouring the skin. Such lifting lessens (and possibly removes altogether) the appearance of the wrinkle. The filament implant 10 can also be implanted under folds and/or sagging skin to lift the skin as desired.

Figure 8A:
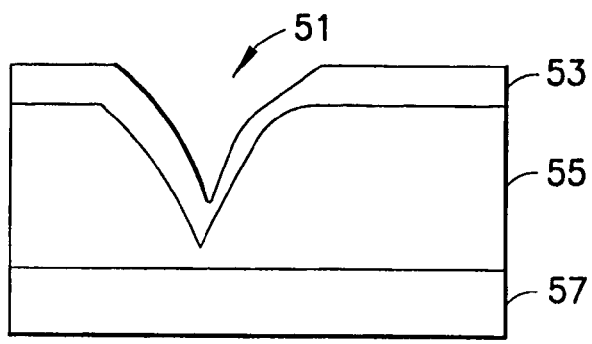
FIGS. 8A through 8C are schematic illustrations of the use of the cosmetic implant systems described herein in lifting the tissue under a wrinkle to lessen the appearance of a wrinkle.
Figure 8B:
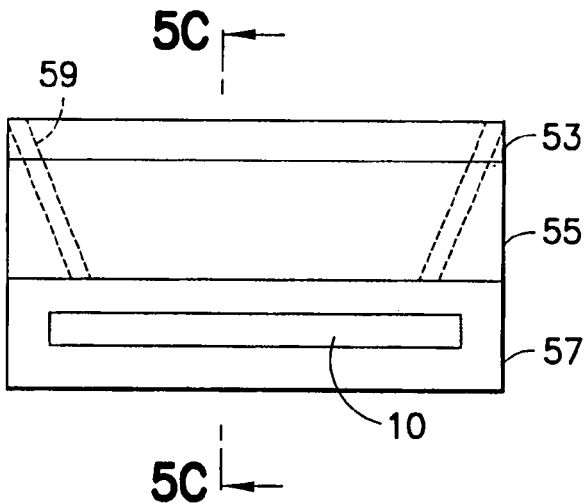
Figure 8C:
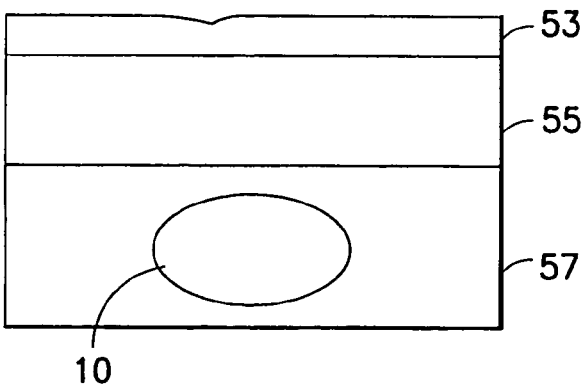

FIGS. 8A-8C illustrate the use of the filament implants described herein in lessening the appearance of a wrinkle 51 that extends into the epidermis layer 53 and dermis layer 55 of skin. The delivery needle is tunneled longitudinally under the wrinkle through the subcutaneous layer 57 to form a passageway 59 through the skin. The filament implant is positioned in the passageway 59 under the wrinkle as shown in FIG. 8B. When delivered by a needle as described above with respect to FIGS. 1-4D, the filament implant is pulled until it is totally under the wrinkle, held in place, and then stretched slightly on each end and cut. In this manner, after being cut the stretched filament retracts back a small distance into the wound under the wrinkle. When implanted under the wrinkle, the filament implant 10 provides a permanent support structure for the tissue above it, thereby lifting and contouring the skin. Such lifting lessens (and possibly removes altogether) the appearance of the wrinkle as best shown in the cross-section schematic of FIG. 8C.

In the embodiments described above, the elastomeric filaments can be made in diameters preferably ranging from 0.1 mm to 1 mm or even larger for very deep wrinkles or other applications. The filament diameter that provides the desired amount of tissue lifting can be selected at the operating table. In addition, the length of the filament is preferably cut to size at the operating table.

The material of the filament implant can be loaded with drugs, such as antibiotics, antiproliferatives and the like, to help prevent infection and mitigate tissue reaction. Further, the filament implant can be made tubular with a lumen where the lumen is filled with a drug reservoir that holds such drugs. Lastly, the material of the filament implant can include a radiopaque filler to enable locating the filament implant under fluoroscopy.

The cross-section of the filament implant can be round, square, rectangular, D-shaped or the like to allow the implant to lie flat below the wrinkle and provide better cosmetic results. Alternatively, the surface of the filament implant can be made scaled or it can have pores or holes in it along the length to help fix or heal in place and further prevent migration. In addition, the surface of the filament implant can be coated with titanium or the like to further allow tissue adhesion and migration prevention.

In addition, for long wrinkles, the filament implant can be tunneled in and out of the length of the wrinkle and either cut where it surfaces, buried in a slot incision, or resubmerge through the same hole.

Furthermore, the needles described herein can be fabricated as a guide wire to help manipulate it through a tortuous path.

There have been described and illustrated herein several embodiments of a polymeric cosmetic implant and corresponding methods of use in cosmetic applications. While particular embodiments of the invention have been described, it is not intended that the invention be limited thereto, as it is intended that the invention be as broad in scope as the art will allow and that the specification be read likewise. Thus, while particular material systems have been disclosed, it will be appreciated that other material systems can be used as well. In addition, while particular configurations and dimensions have been disclosed, it will be appreciated that other configurations and dimension could be used as well. It will therefore be appreciated by those skilled in the art that yet other modifications could be made to the provided invention without deviating from its spirit and scope as claimed.

What is claimed is:

1. A cosmetic surgical method comprising:
   providing an elastomeric filament having an elasticity along its length of at least 200 percent; and
   implanting the elastomeric filament under the surface of the skin such that the elastomeric filament extends substantially lengthwise under a wrinkle to thereby lift the skin and lessen the appearance of the wrinkle;
   wherein said elastomeric filament has a middle portion extending between opposed ends, and said filament is held in place by applying pressure to the skin above said middle portion, and is stretched and cut at each of said opposed ends whereby after being cut, each of said opposed ends of said filament retracts back inward and under the wrinkle due to the elastomeric nature of said filament.

2. A cosmetic surgical method according to claim 1; wherein:
   the elasticity of said elastomeric filament is between 200 percent and 1500 percent.

3. A cosmetic surgical method according to claim 1, wherein:
   the elastomeric filament is implanted utilizing a needle adapted to tunnel through the skin with the filament secured to the needle.

4. A cosmetic surgical method according to claim 1, wherein:
   said elastomeric filament has a maximal dimension in a range between 0.1 mm and 1 mm.

5. A cosmetic surgical method according to claim 1, wherein:
   the material of the elastomeric filament is loaded with a drug.

6. A cosmetic surgical method according to claim 5, wherein:
   said drug comprises one of an antibiotic agent and an antiproliferative agent.

7. A cosmetic surgical method according to claim 5, wherein:
   the elastomeric filament is tubular with a lumen that forms a drug reservoir that holds such drug.

8. A cosmetic surgical method according to claim 1, wherein:
   said elastomeric filament comprises a radiopaque filler to enable locating said filament under fluoroscopy.

9. A cosmetic surgical method according to claim 1, wherein:
   said elastomeric filament has a cross-section selected from the group consisting of: round, square, rectangular, and D-shaped.

10. A cosmetic surgical method according to claim 1, wherein:
    said elastomeric filament is realized from a material selected from the group consisting of: silicon rubber; expanded polytetrafluorethelyene (ePTFE); polyurethane; polyolefin; copolymers of nylon; copolymers of polyester; elastin; and a polyolefinic copolymer material having a triblock polymer backbone comprising polystyrene-polyisobutylene-polystyrene.

11. A cosmetic surgical method according to claim1, wherein:
    said elastomeric filament is realized from a polyolefinic copolymer material having a triblock polymer backbone comprising polystyrene-polyisobutylene-polystyrene.

12. A cosmetic surgical method according to claim 1, wherein:
    said elastomeric filament is implanted to extend substantially through the subcutaneous layer of the skin along the length of the wrinkle.

* * * * *